United States Patent [19]
Miyazawa et al.

[11] Patent Number: 5,606,039
[45] Date of Patent: Feb. 25, 1997

[54] ETOPOSIDE PHOSPHATE AND PREPARATIVE INTERMEDIATES

[75] Inventors: Yoshinobu Miyazawa; Hitoshi Sato, both of Saitama-ken; Hiroshi Yoshikawa, Fujioka; Kouichi Ohkawa, Chiba; Noriko Tomiyoshi, Tokyo, all of Japan

[73] Assignee: Nippon Kayaku Kabushiki Kaisha, Tokyo, Japan

[21] Appl. No.: 410,811

[22] Filed: Mar. 27, 1995

Related U.S. Application Data

[62] Division of Ser. No. 43,993, Apr. 8, 1993, abandoned.

[30] Foreign Application Priority Data

Apr. 24, 1992 [JP] Japan ................... 4-129764

[51] Int. Cl.$^6$ ........................... C07H 15/24
[52] U.S. Cl. ........................ 536/17.1; 536/18; 536/18.2; 536/18.4
[58] Field of Search ................... 536/4.1, 17.1, 536/18.1, 18.6, 115, 120, 124, 18.2, 18.4

[56] References Cited

U.S. PATENT DOCUMENTS

| | | | |
|---|---|---|---|
| 4,564,675 | 1/1986 | Kurabayashi et al. | 536/18.1 |
| 4,757,138 | 7/1988 | Fujii et al. | 536/18.1 |
| 4,904,768 | 2/1990 | Saulnier et al. | 536/17.1 |
| 5,036,055 | 7/1991 | Ohnuma et al. | 514/27 |
| 5,041,424 | 8/1991 | Saulnier et al. | 514/27 |
| 5,081,234 | 1/1992 | Ohnuma et al. | 536/17.1 |
| 5,206,350 | 4/1993 | Wang et al. | 536/18.1 |

FOREIGN PATENT DOCUMENTS

| | | |
|---|---|---|
| 0511563 | 11/1992 | European Pat. Off. . |
| 3192793 | 8/1988 | Japan . |
| 63-192793 | 8/1988 | Japan . |
| 2207674 | 2/1989 | United Kingdom . |

OTHER PUBLICATIONS

Derwent Abstract of JP Laid-Open No. Shou 63–192,793.

Ramirez et al., "Amine Catalysis in Phosphoryl Transfer From 2,4–Diniutrophenyl Phosphate in Aprotic and Protic Solvents," *Tetrahedron*, 35(13), 1581–1589 (1979).

Ogawa et al., "Studies on Metal–Nucleotides Complexes. IV. Studies on the Isolated Metal–Inosinic Acid (5'–IMP) Complexes by Infrared Absorption Spectra," *Chem. Pharm. Bull.*, 19(8), 1650–1655 (1971).

*Primary Examiner*—John Kight
*Assistant Examiner*—L. Eric Crane
*Attorney, Agent, or Firm*—Nields & Lemack

[57] ABSTRACT

An etoposide phosphate represented by the formula (1):

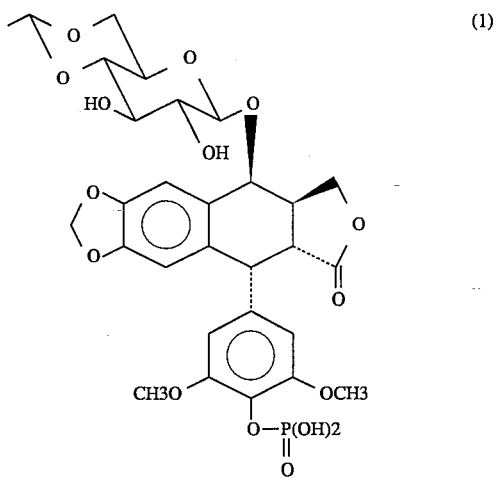

is prepared by blocking the hydroxyl groups of the saccharide moiety of etoposide with halogenoacetyl groups, thereafter phosphorylating the 4'-position, and removing the halogenoacetyl groups from the obtained phosphate in the presence of an amine.

This process can give the objective etoposide phosphate in a higher yield than that of the prior art to enable the industrial mass-production thereof.

10 Claims, No Drawings

ETOPOSIDE PHOSPHATE AND PREPARATIVE INTERMEDIATES

This application is a divisional of application Ser. No. 08/043,993 filed Apr. 8, 1993, now abandoned.

BACKGROUND OF THE INVENTION

1. Field of the Invention

The present invention relates to a process for the preparation of etoposide phosphate and intermediates thereof.

2. Description of the Prior Art

Etoposide phosphate is a useful compound having an antitumor activity, which is improved in water-solubility as compared with etoposide. Processes for the preparation thereof have been reported in Japanese Patent Laid-Open No. 192793/1988 and U.S. Pat. No. 4,904,768.

The process disclosed in the U.S. Pat. No. 4,904,768 comprises reacting etoposide directly with phosphorus oxychloride or an alkyl or aryl chlorophosphate, and therefore gives a large amount of by-products by the reaction of such a phosphorus compound with the hydroxyl groups of the saccharide moiety in addition to the objective compound wherein the phosphorus compound is bonded to the 4'-position of etoposide. Accordingly, the reaction mixture obtained by the process must be subjected to specific treatment such as column chromatography to remove the by-products. On the other hand, the process disclosed in the Japanese Patent Laid-Open No. 192793/1988 uses etoposide wherein the hydroxyl groups of the saccharide moiety are blocked, and therefore gives little by-products. However, the process involves the use of acetic acid and zinc in the deblocking of the saccharide moiety and necessitates the isolation of the objective etoposide phosphate by lyophilization, thus being problematic in conducting mass-production.

SUMMARY OF THE INVENTION

The present invention relates to a process for the preparation of an etoposide phosphate represented by the formula (1):

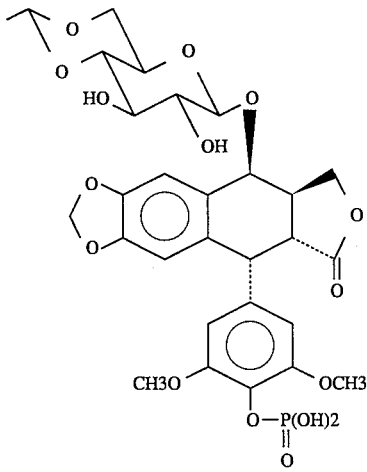

which comprises freeing a compound represented by the general formula (2):

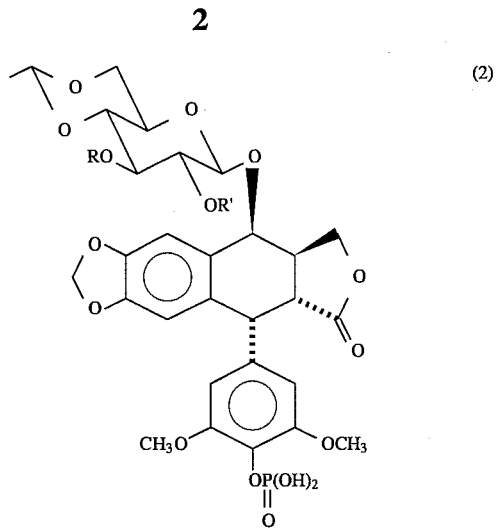

wherein R and R' may be the same or different from each other and each represent a group represented by the formula: $-COCH_mX_{(3-m)}$ (wherein X represents a halogen atom and m is an integer of 0 to 2), from the R and R' groups in the presence of an amine, and to compounds represented by the general formula (2) and to compounds represented by the following general formula (3):

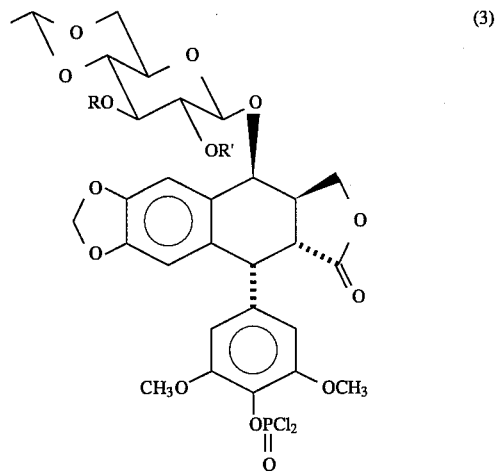

wherein R and R' are each as defined above.

The process of the present invention is characterized by using a halogenoacetyl group as the protective group for the saccharide moiety and conducting the elimination of the group in the presence of an amine, particularly a tertiary amine, to thereby enable the preparation of the etoposide phosphate in a higher yield than that of the prior art, thus being suitable for industrial mass-production.

DETAILED DESCRIPTION OF PREFERRED EMBODIMENTS

In the general formulae (2) and (3), R and R' are each selected from among monohalogenoacetyl, dihalogenoacetyl and trihalogenoacetyl groups (hereinafter abbreviated generically to "halogenoacetyl group"). The halogen atom as defined with respect to X in the R and R' groups includes fluorine, chlorine, bromine and iodine atoms.

More detailed description will now be made on the process for the preparation according to the present invention.

A compound represented by the general formula (2) is freed from halogenoacetyl groups which block the hydroxyl groups of the saccharide moiety through solvolysis in a solvent selected from among alcohols such as methanol and ethanol, halogenated hydrocarbons such as methylene chloride and chloroform, and ethers such as tetrahydrofuran and dioxane, or a mixture of two or more of them in the presence of a suitable amine or amine salt. The amine may be any of a ($C_1$-$C_5$) alkylamine selected from among primary amines such as monomethylamine and monoethylamine, secondary amines such as dimethylamine, diethylamine and ethylmethylamine, and tertiary amines such as trimethylamine and triethylamine and an aromatic amine selected from among aniline, diethylphenylamine and so on. The use of a tertiary($C_1$-$C_5$)alkylamine, e.g., triethylamine is preferable in virtue of its slow epimerization. The amine salt may be one of a primary, secondary, tertiary or aromatic amine with an organic acid such as acetic acid. The solvolysis includes hydrolysis, alcoholysis, ammonolysis and aminolysis. The reagent to be used in the solvolysis includes water, the above alcohols, ammonia, and the above primary and secondary amines. When a tertiary amine or an amine salt is used, it is preferable that the solvent to be used be an alcohol such as methanol or ethanol or a mixture of an alcohol with other solvent. When an amine is used, the elimination of the halogenoacetyl group can be easily conducted at 0° to 70° C., preferably at 0° to 30° C. and the amount of the amine to be used is 0.2 to 15 equivalents, preferably 1 to 3 equivalents based on the compound of the general formula (2), while when an amine salt is used, the elimination can be easily conducted at 20° to 70° C., preferably at 30° to 50° C. and the amount of the salt to be used is 1 to 15 equivalents, preferably 3 to 10 equivalents based on the compound of the general formula (2). The reaction is completed in about 1 to 6 hours.

After the completion of the reaction, the reaction mixture is neutralized with hydrogen chloride/tetrahydrofuran and concentrated, followed by the solvent replacement by tetrahydrofuran. The resulting mixture is filtered to remove a formed amine hydrochloride. The filtrate is concentrated, followed by the addition of n-hexane. The obtained mixture was cooled to give the objective etoposide phosphate.

The compound of the general formula (2) to be used as the starting material in the present invention can be prepared as follows.

The 4'-position of 4'-demethylepipodophyllotoxin is blocked with a group which is easily removable by catalytic reduction using a palladium catalyst or the like, for example, a substituted or unsubstituted benzyloxycarbonyl group. Examples of the substituted benzyloxycarbonyl group include p-methoxybenzyloxycarbonyl, p-nitrobenzyloxycarbonyl and p-chlorobenzyloxycarbonyl groups. The 4'-dimetylepipodophyllotoxin thus blocked is coupled with β-D-2,3-di-O-halogenoacetyl-4,6-O-ethylideneglucopyranose in the presence of a boron trifluoride-ether complex in a conventional manner.

The β-D-2,3-di-O-halogenoacetyl-4,6-O-ethylideneglucopyranose to be used in the above coupling reaction can be prepared by the process disclosed in U.S. Pat. No. 4,757,138 or 4,564,675.

After the completion of the coupling reaction, the obtained product is hydrogenated in the presence of a palladium catalyst to remove the 4'-protective group, by which a 4'-demethylepipodophyllotoxin β-D-2,3-di-O-halogenoacetyl-4,6-O-ethylideneglycoside is obtained. This compound is further reacted with phosphorus oxychloride in an aprotic solvent such as tetrahydrofuran, dioxane, acetone, acetonitrile, chloroform, methylene chloride or 1,2-dichloroethene in the presence of a suitable base to form a 4'-O-dichlorophosphoryl-4'-demethylepipodophyllotoxin β-D-2,3-di-O-halogenoacetyl-4,6-O-ethylideneglycoside represented by the above general formula (3). The base to be used in this step is a tertiary amine, pyridine or the like which are unreactive with the product.

The reaction mixture or the isolated compound of the general formula (3) is subjected to the hydrolysis of the dichlorophosphoryl group in water in the presence of a suitable base under the neutral or acidic condition, by which a 4'-O-phosphono-4'-demethylepipodophyllotoxin β-D-2,3-di-O-halogenoacetyl-4,6-O-ethylideneglycoside represented by the general formula (2) is obtained. The base to be used in the hydrolysis is a tertiary amine or aromatic amine such as pyridine which are unreactive with the compound of the general formula (3). The halogenoacetyl groups which block the hydroxyl groups of the saccharide moiety are stable under the above hydrolysis conditions for the dichlorophosphoryl group. After the completion of the hydrolysis, the pH of the reaction mixture is adjusted to 1.0 to 2.5 to extract the compound of the general formula (2) from the aqueous phase into an organic phase. This organic phase is concentrated, followed by the addition of n-hexane. Thus, the compound of the general formula (2) is isolated.

EXAMPLE 1

(1) Synthesis of 4'-O-dichlorophosphoryl-4'-demethylepipodophyllotoxin β-D-2,3-di-O-dichloroacetyl-4,6-O-ethylideneglycoside 22.03 g (27.18 mmol) of 4'-demethylepipodophyllotoxin β-D-2,3-di-O-dichloroacetyl-4,6-O-ethylideneglycoside was dissolved in 190 ml of tetrahydrofuran. The obtained solution was cooled to −15° C. 8.34 g (54.4 mmol) of phosphorus oxychloride was dropped into the resulting solution, followed by the dropwise addition of 8.25 g (81.5 mmol) of triethylamine.

The obtained mixture was reacted at −10° to −15° C. and filtered to remove formed triethylamine hydrochloride. The filtrate was concentrated to 60 g, followed by the addition of 500 ml of isopropyl ether. The obtained mixture was cooled to precipitate crystals. The crystals were recovered by filtration to give 4'-O-dichlorophosphoryl-4'-demethylepipodophyllotoxin β-D-2,3-di-O-dichloroacetyl-4,6-O-ethylideneglycoside.

dry weight of product: 24.45 g (yield: 97%)

200 MHz 1H NMR (DMSOd-6) δ 1.21 (d, 3H), 2.85–3.10 (m, 2H), 3.59 (s, 6H), 3.41–3.84 (m, 3H), 4.19 (m, 2H), 4.32 (m, 1H), 4.53 (d, 1H), 4.79 (q, 1H),4.98 (m, 2H), 5.30 (d 1H), 5.54 (t, 1H), 6.01 (s, 1H), 6.05 (s, 1H), 6.19 (s, 2H), 6.54 (s, 1H), 6.66 (s, 1H), 6.99 (s, 1H), 7.01 (s, 1H)

MS (FAB), m/e, 927 (M+H )

(2) Synthesis of 4'-O-phosphono-4'-demethylepipodophyllotoxin β-D-2,3-di-O-dichloroacetyl-4,6-O-ethylideneglycoside 24.4 g (26.37 mmol) of 4'-O-dichlorophosphoryl-4'-demethylepipodophyllotoxin β-D-2,3-di-O-dichloroacetyl-4,6-O-ethylideneglycoside was added to ml of water. 12.28 g of pyridine was dropped into the mixture at 0° to 5° C. to conduct hydrolysis. After the completion of the hydrolysis, 180 ml of chloroform was added to the reaction mixture and the pH of the resulting mixture was adjusted to 2 with 6N hydrochloric acid to extract a product with the chloroform.

The chloroform phase was washed with 120 ml of a saturated aqueous solution of common salt and concentrated, followed by the addition of 360 ml of n-hexane. Thus, 4'-O-phosphono-4'-demethylepipodophyllotoxin β-D-2,3-di-O-dichloroacetyl-4,6-O-ethylideneglycoside was obtained.

dry weight of product: 22.99 g (yield: 97.9%)

200 MHz 1H NMR (DMSOd-6) δ 1.21 (d, 3H), 2.83–3.10 (m, 2H), 3.57 (s, 6H), 3.48–3.85 (m, 3H), 4.18 (m, 2H), 4.33 (m, 1H), 4.51 (d, 1H), 4.78 (q, 1H), 4.98 (m, 2H), 5.27 (d, 1H), 5.54 (t, 1H), 6.00 (s, 1H), 6.04 (s, 1H), 6.16 (s, 2H), 6.54 (s, 1H), 6.63 (s, 1H), 6.94 (s, 1H), 7.01 (s, 1H)

MS (FAB), m/e, 891 (M+H)

(3) Synthesis of Etoposide Phosphate (of the formula (1))

22.99 g (25.82 mmol) of 4'-O-phosphono-4'-demethyl epipodophyllotoxin β-D-2,3-di-O-dichloroacetyl-4,6-O-ethylideneglycoside was dissolved in 150 ml of methanol and the obtained solution was cooled to 5° to 10° C., followed by the dropwise addition of 5.22 g (51.64 mmol) of triethylamine.

The obtained mixture was reacted at 10° C. After the completion of the reaction, the reaction mixture was neutralized and adjusted to pH 2.5–3.0 with hydrogen chloride/tetrahydrofuran. The resulting solution was concentrated to dryness and tetrahydrofuran was added to the residue to conduct solvent replacement. The obtained tetrahydrofuran solution was adjusted to pH 1.0 with hydrogen chloride/tetrahydrofuran to precipitate triethylamine hydrochloride. The triethylamine hydrochloride was filtered out and the filtrate was concentrated, followed by the addition of 200 ml of n-hexane. The obtained mixture was stirred and the supernatant liquid was removed, followed by the addition of 200 ml of n-hexane. This procedure was repeated several times to give etoposide phosphate as a solid, which was recovered by filtration.

dry weight of product: 11.22 g (yield: 65%) (yield based on the raw material used in the step (1): 61.7%)

200 MHz 1H NMR (DMSOd-6) δ 1.25 (d, 3H), 2.80–3.00 (m, 1H), 3.61 (s, 6H), 3.02–3.66 (m, 6H), 4.04 (dd, 1H), 4.24 (d, 2H), 4.55–4.59 (m, 2H), 4.72 (q, 1H), 4.95 (d, 1H), 5.23 (br, 2H), 6.03 (s, 2H), 6.23 (s, 2H), 6.53 (s, 1H), 7.01 (s, 1H)

MS (FAB), m/e, 669 (M+H)

EXAMPLE 2

(1) Synthesis of 4'-O-dichlorophosphoryl-4'-demethylepipodophyllotoxin β-D-2,3-di-O-dichloroacetyl-4,6-O-ethylideneglycoside 9.5 g (11.72 mmol) of 4'-demethylepipodophyllotoxin β-D-2,3-di-O-dichloroacetyl-4,6-O-ethylideneglycoside was dissolved in 80 ml of tetrahydrofuran and the obtained solution was cooled to −5° C. 3.6 g (35.6 mmol) of triethylamine was added to the resulting solution, followed by the dropwise addition of 3.6 g (23.5 mmol) of phosphorus oxychloride. The obtained mixture was reacted at −5° to −15° C.

(2) Synthesis of 4'-O-phosphono-4'-demethylepipodophyllotoxin β-D-2,3-di-O-dichloroacetyl-4,6-O-ethylideneglycoside The above reaction mixture containing 4'-O-dichlorophosphoryl-4'-demethylepipodophyllotoxin β-D-2,3-di-O-dichloroacetyl-4,6-O-ethylideneglycoside was added to 225 ml of water. 5.8 g of pyridine was dropped into the obtained mixture at 25° C. to conduct hydrolysis. After the completion of the hydrolysis, 85 ml of methylene chloride was added to the reaction mixture and then the mixture was adjusted to pH 1 with 6N hydrochloric acid to extract a reaction product with the methylene chloride. The methylene chloride phase was concentrated to 30 ml.

(3) Synthesis of etoposide phosphate (of the formula (1))

65 ml of methanol was added to the concentrate obtained above containing 4'-phosphono-4'-demethylepipodophyllotoxin β-D-2,3-di-O-dichloroacetyl-4,6-O-ethylideneglycoside, followed by the dropwise addition of 2.37 g (23.4 mmol) of triethylamine at room temperature.

The obtained mixture was reacted at room temperature for 4 hours. After the completion of the reaction, the reaction mixture was neutralized and adjusted to pH 3 with hydrochloric acid/tetrahydrofuran. The resulting solution was concentrated to dryness and tetrahydrofuran was added to the residue to conduct solvent replacement. The obtained tetrahydrofuran solution was adjusted to pH 0.5 with hydrochloric acid/tetrahydrofuran to precipitate formed triethylamine hydrochloride. The triethylamine hydrochloride was filtered out and the filtrate was concentrated, followed by the addition of 200 ml of n-hexane. The obtained mixture was stirred and the supernatant liquid was removed, followed by the addition of 200 ml of n-hexane. This procedure was repeated several times to give etoposide phosphate as a solid, which was recovered by filtration.

dry weight of product: 5–36 g (yield based on the raw material used in the step (1): 68.4%) picro isomer content in the reaction mixture: 0.6%

EXAMPLE 3

(1) Synthesis of 4'-O-dichlorophosphoryl-4'-demethylepipodophyllotoxin β-D-2,3-di-O-dichloroacetyl-4,6-O-ethylideneglycoside 9.5 g (11.72 mmol) of 4'-demethylepipodophyllotoxin β-D-2,3-di-O-dichloroacetyl-4,6-O-ethylideneglycoside was dissolved in 80 ml of tetrahydrofuran. The obtained solution was cooled to −5° C. 3.6 g (35.6 mmol) of triethylamine was added to the resulting solution, followed by the dropwise addition of 3.6 g (23.5 mmol) of phosphorus oxychloride. The obtained mixture was reacted at −5° to −15° C.

(2) Synthesis of 4'-O-phosphono-4'-demethylepipodophyllotoxin β-D-2,3-di-O-dichloroacetyl-4,6-O-ethylideneglycoside The reaction mixture obtained above containing 4'-O-dichlorophosphoryl-4'-demethylepipodophyllotoxin β-D-2,3-di-O-dichloroacetyl-4,6-O-ethylideneglycoside was added to 225 ml of water. 5.3 g of pyridine was dropped into the obtained mixture at 25° C. to conduct hydrolysis. After the completion of the hydrolysis, 85 ml of methylene chloride was added to the reaction mixture and then the mixture was adjusted to pH 1 with 6N hydrochloric acid to extract a reaction product with the methylene chloride. The methylene chloride phase was concentrated to 35 ml.

(3) Synthesis of Etoposide Phosphate (of the formula (1))

65 ml of methanol was added to the resulting concentrate containing 4'-O-phosphono-4'-demethylepipodophyllotoxin β-D-2,3-di-O-dichloroacetyl-4,6-O-ethylideneglycoside, followed by the dropwise addition of 1.71 g (23.4 mmol) of diethylamine at room temperature.

The obtained mixture was reacted at room temperature for 4 hours. After the completion of the reaction, the reaction mixture was neutralized and adjusted to pH 3 with hydrogen chloride/tetrahydrofuran. The resulting solution was concentrated to dryness and tetrahydrofuran was added to the residue to conduct solvent replacement. The obtained tetrahydrofuran solution was adjusted to pH 1.0 with hydrochloric acid/tetrahydrofuran to precipitate formed diethylamine hydrochloride. This diethylamine hydrochloride was filtered out and the filtrate was concentrated, followed by the addition of 200 ml of n-hexane. The obtained mixture was stirred and the supernatant liquid was removed, followed by the addition of 200 ml of n-hexane. This procedure was repeated several times to give etoposide phosphate as a solid, which was recovered by filtration.

dry weight of product: 4.98 g (yield based on the raw material used in the step (1): 63.5%) picro isomer content in the reaction mixture: 3.3%

EXAMPLE 4

(1) Synthesis of 4'-O-dichlorophosphoryl-4'-demethylepipodophyllotoxin β-D-2,3-di-O-dichloroacetyl-4,6-O-ethylideneglycoside 9.5 g (11.72 mmol) of 4'-demethylepipodophyllotoxin β-D-2,3-di-O-dichloroacetyl-4,6-O-ethylideneglycoside was dissolved in 80 ml of tetrahydrofuran. The obtained solution was cooled to −5° C. 3.6 g (35.6 mmol) of triethylamine was added to the resulting solution, followed by the dropwise addition of 3.6 g (23.5 mmol) of phosphorus oxychloride. The obtained mixture was reacted at −5° to −15° C.

(2) Synthesis of 4'-O-phosphono-4'-demethylepipodophyllotoxin β-D-2,3-di-O-dichloroacetyl-4,6-O-ethylideneglycoside The reaction mixture obtained above containing 4'-O-dichlorophosphoryl-4'-demethylepipodophyllotoxin β-D-2,3-di-O-dichloroacetyl-4,6-O-ethylideneglycoside was added to 225 ml of water. 5.8 g of pyridine was dropped into the obtained mixture at 25° C. to conduct hydrolysis. After the completion of the hydrolysis, 85 ml of methylene chloride was added to the reaction mixture and then the mixture was adjusted to pH 1 with 6N hydrochloric acid to extract a reaction product with the methylene chloride. The methylene chloride phase was concentrated to 25 ml.

(3) Synthesis of Etoposide Phosphate (of the formula 65 ml of methanol was added to the resulting concentrate containing 4'-O-phosphono-4'-demethylepipodophyllotoxin β-D-2,3-di-O-dichloroacetyl-4,6-O-ethylideneglycoside, followed by the dropwise addition of 1.39 g (23.5 mmol) of isopropylamine at room temperature.

The obtained mixture was reacted at room temperature for 4 hours. After the completion of the reaction, the reaction mixture was neutralized and adjusted to pH 3 with hydrogen chloride/tetrahydrofuran. The resulting solution was concentrated to dryness and tetrahydrofuran was added to the residue to conduct solvent replacement. The obtained tetrahydrofuran solution was adjusted to pH 0.6 with hydrochloric acid/tetrahydrofuran to precipitate formed isopropylamine hydrochloride. This isopropylamine hydrochloride was filtered out and the filtrate was concentrated, followed by the addition of 200 ml of n-hexane. The obtained mixture was stirred and the supernatant liquid was removed, followed by the addition of 200 ml of n-hexane. This procedure was repeated several times to give etoposide phosphate as a solid, which was recovered by filtration.

dry weight of product: 4.33 g (yield based on the raw material used in the step (1): 55.3%) picro isomer content in the reaction mixture: 2.5%

REFERENTIAL EXAMPLE

Synthesis of 4'-demethylepipodophyllotoxin β-D-2,3-di-O-dichloroacetyl-4,6-O-ethylideneglycoside

(1) Synthesis of 4'-O-benzyloxycarbonyl-4'-demethylepipodophyllotoxin 22 g (55 mmol) of 4'-demethylepipodophyllotoxin was added to 220 ml of methylene chloride. The obtained mixture was cooled to 0° C., followed by the addition of 7,35 g (72.6 mmol) of triethylamine and 11.25 g (66 mmol) of benzyloxycarbonyl chloride. The obtained mixture was reacted at 0° to 5° C. for 2 hours. After the completion of the reaction, the methylene chloride phase was washed with water and concentrated. 40 ml of acetone was added to the obtained concentrate to form a solution. 350 ml of methanol was added to the solution to precipitate 4'-O-benzyloxycarbonyl-4'-demethylepipodophyllotoxin, which was filtered and dried.

dry weight of product: 22.05 g (yield: 75.1%)

(2) Synthesis of 4'-demethylepipodophyllotoxin β-D 2,3-di-O-dichloroacetyl-4,6-O-ethylideneglycoside 17.0 g (31.8 mmol) of 4'-O-benzyloxycarbonyl-4'-demethylepipodophyllotoxin and 17.65 g (41.2 mmol) of β-D-2,3-di-O-dichloroacetyl-4,6-O-ethylideneglucopyranose were dissolved in 240 ml of methylene chloride. The obtained solution was cooled to −20° C. and 6.77 g (47.7 mmol) of boron trifluoride etherate was added to the solution to conduct coupling reaction. After the completion of the reaction, 58.5 g (57.2 mmol) of pyridine was added to the reaction mixture. The obtained solution was washed successively with delute hydrochloric acid, an aqueous solution of sodium hydrogencarbonate and water, and the methylene chloride phase was concentrated. 100 ml of acetone was added to the concentrate to form a solution, followed by the addition of 1.6 g of palladium black. Hydrogen was introduced into the obtained mixture to conduct debenzyloxycarbonylation. After the completion of the reaction, the reaction mixture was filtered to remove the catalyst and the filtrate was concentrated. 130 ml of isopropyl ether was added to the concentrate to precipitate 4'-demethylepipodophyllotoxin β-D-2,3-di-O-dichloroacetyl-4,6-O-ethylideneglycoside as a crystal. This crystal was recovered by filtration and dried.

dry weight of product: 22.03 g (yield: 85.5%)

What is claimed is:

1. A compound represented by the general formula (2):

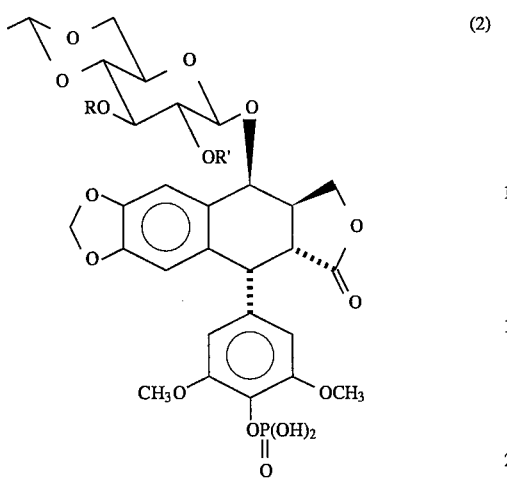

wherein R and R' may be the same or different from each other and each represents a group represented by the formula: —$COCH_mX_{(3-m)}$ (wherein X represents a halogen atom and m is an integer of 0 to 2).

2. A compound as set forth in claim 1, wherein the halogen atom is a chlorine atom.

3. A compound as set forth in claim 1, , wherein R and R' are each a dichloroacetyl group.

4. A compound as set forth in claim 1, wherein R and R' are each a monochloroacetyl group.

5. A compound as set forth in claim 1, wherein R and R' are each a trichloroacetyl group.

6. A compound represented by the general formula (3):

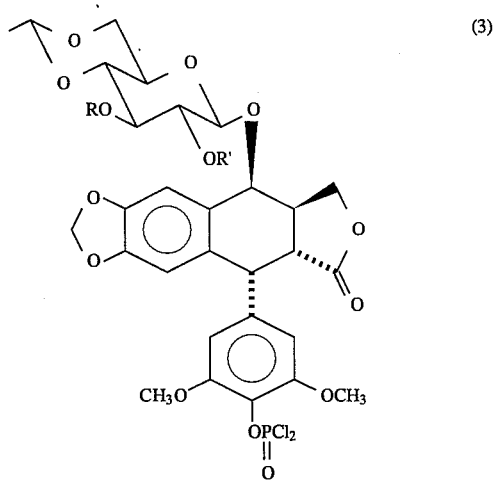

wherein R and R' may be the same or different from each other and each represents a group represented by the formula: —$COCH_mX_{(3-m)}$ (wherein X represents a halogen atom and m is an integer of 0 to 2).

7. A compound as set forth in claim 6, wherein the halogen atom is a chlorine atom.

8. A compound as set forth in claim 6, wherein R and R' are each a dichloroacetyl group.

9. A compound as set forth in claim 6, wherein R and R' are each a monochloroacetyl group.

10. A compound as set forth in claim 6, wherein R and R' are each a trichloroacetyl group.

* * * * *